United States Patent [19]

Buysch et al.

[11] 4,083,870

[45] Apr. 11, 1978

[54] PROCESS FOR CONVERTING POLYAMINOPOLYARYL-METHANES INTO DIAMINODIARYLMETHANES

[75] Inventors: Hans-Josef Buysch, Krefeld; Peter Ziemek, Cologne; Roderich Raue, Leverkusen, all of Germany

[73] Assignee: Bayer Aktiengesellschaft, Leverkusen, Germany

[21] Appl. No.: 441,930

[22] Filed: Feb. 12, 1974

[30] Foreign Application Priority Data

Feb. 17, 1973 Germany .............................. 2307684

[51] Int. Cl.$^2$ ................................................ C07C 85/24
[52] U.S. Cl. ........................... 260/570 D; 260/2.5 AC; 260/453 AM
[58] Field of Search ..................... 260/570 D

[56] References Cited

U.S. PATENT DOCUMENTS 3,857,890   12/1974   Recchia et al. ...................... 260/570

FOREIGN PATENT DOCUMENTS

| 107,718 | 12/1899 | Germany ............................. 260/570 |
| 2,135,347 | 2/1973 | Germany ............................. 260/570 |
| 1,127,347 | 9/1968 | United Kingdom ................ 260/570 |
| 1,169,127 | 10/1969 | United Kingdom ................ 260/570 |

*Primary Examiner*—Robert V. Hines
*Attorney, Agent, or Firm*—Gene Harsh; Joseph C. Gil

[57] ABSTRACT

Polyaminopolyarylmethanes and an aromatic monoamine unsubstituted in an ortho or a para position to the amino group are heated in water to produce diaminodiarylmethanes.

4 Claims, No Drawings

PROCESS FOR CONVERTING POLYAMINOPOLYARYL-METHANES INTO DIAMINODIARYLMETHANES

This invention relates generally to amines and more particularly to a new process for converting polyaminopolyarylmethanes into diaminodiarylmethanes by decomposition with aromatic monoamines.

It is known that diaminodiphenylmethanes can be prepared by reacting aromatic amines with formaldehyde or with compounds which split off formaldehyde, the reaction being carried out in the presence of acid catalysts or without catalysts (German Offenlegungsschrift No. 2,118,490). The reaction is invariably accompanied by the formation of considerable quantities of polyaminopolyphenylmethanes which remain behind as a sump-product or still bottoms when the reaction mixture is worked up in the usual way by distillation. These trinuclear and higher nuclear polyaminopolyphenylmethanes are complex mixtures for which there is only a limited utility for technical application, for example, as intermediate products for the production of the corresponding polyisocyanate mixtures. The corresponding diaminodiphenylmethanes, on the other hand, are valuable starting materials for production of the corresponding diisocyanates useful for making polyurethanes and the like and there is, therefore, a technical need for a process by which trinuclear and higher nuclear polyaminopolyphenylmethanes can be converted into the corresponding diaminodiphenylmethanes.

In United States Patent Application, Ser. No. 270,918 and now abandoned there has been disclosed a process for converting polyaminopolyarylmethanes into diaminodiarylmethanes by heating a mixture of polyaminopolyarylmethanes and monoarylamines in the presence of solid acid catalysts which are insoluble in the reaction mixture.

The products obtained by the process disclosed in the United States Patent Application, however, are contaminated with considerable proportions of by-products which do not contain any aromatically bound amino groups. This is a serious disadvantage, especially for the production of diaminodiphenylmethanes which are used as starting materials for the production of the corresponding diisocyanates, because the by-products are not available for the phosgenation reaction conventionally carried out to form the corresponding isocyanates but give rise to other by-products which are modified as a result of the action of phosgene. These modified by-products have the unpleasant property of being lachrymatory and in addition they cause rapid inactivation of the catalysts or activators normally used for the production of polyurethane foams.

It is, therefore, an object of this invention to provide a process for converting polyaminopolyarylmethanes into diaminodiarylmethanes which is devoid of the disadvantages of the aforesaid prior art process. Another object of the invention is to provide a process for converting polyaminopolyarylmethanes into diaminodiarylmethanes which are suitable for phosgenation to produce the corresponding diisocyanates. A more specific object of the invention is to provide a process for converting the polyaminopolyarylmethanes remaining after distillation of the reaction products obtained when formaldehyde and aniline are condensed to produce amines for phosgenation into the corresponding organic polyisocyanates. A still further object of the invention is to provide a process for converting 4,4'-diphenylmethane diamine into the 2,4'-isomers.

The foregoing objects and others are accomplished in accordance with this invention, generally speaking, by providing a process wherein a polyaminopolyarylmethane and an aromatic monoamine unsubstituted in one ortho or in the para position to the amino groups are heated in a liquid phase in the presence of water at a temperature above 220° C. It has now surprisingly been found that production of diaminodiarylmethanes from trinuclear and higher nuclear polyaminopolyarylmethanes can be carried out substantially free from the above mentioned disadvantages of the known process of the art if the reaction between polyaminopolyarylmethanes and the aromatic monoamine is carried out in the liquid phase in the presence of water at temperatures above 220° C. Moreover, this new process does not require the catalysts used in the process according to United States Patent Application Ser. No. 270,918 and now abandoned.

This invention, therefore, relates to a process for the production of diaminodiarylmethanes which contain an increased proportion of 2,4'-diaminodiarylmethanes by heating polyaminopolyarylmethanes in the liquid phase with aromatic monoamines which contain at least one free position in the ortho- or para-position to the amino group, characterized in that the reaction is carried out in the presence of water. The diaminodiarylmethanes provided by the invention can be converted into the corresponding diisocyanates for use in making polyurethane foams for heat insulation or other known products.

The starting materials used in the process according to the invention are mixtures of polyaminopolyarylmethanes of the general formula

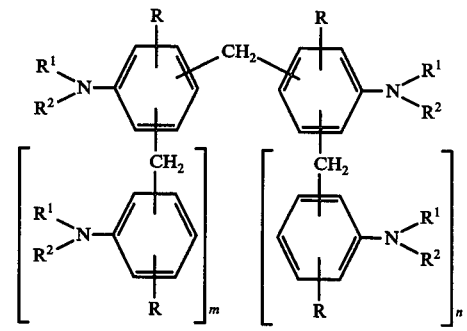

in which
  $n$ represents an integer of from 0 to 2,
  $m$ represents an integer of from 0 to 2,
  R represents hydrogen, a halogen atom, an alkyl group containing 1-4 carbon atoms, an alkoxy group containing 1-4 carbon atoms, an aralkyl group containing 7-10 carbon atoms or a condensed benzene ring, and
  $R^1$ and $R^2$, which may be the same or different, represent hydrogen, an alkyl group containing 1-4 carbon atoms or a phenyl group.

The polyaminopolyarylmethanes of the above general formula used for the process according to the invention are preferably those in which R, $R^1$ and $R^2$ represent hydrogen.

The general formula for polyarylamines shown above serves to represent the mixture known per se which is normally obtained by the known process of arylamine/- formaldehyde condensation, the individual components of which substantially conform to this general formula. Preparation of the polyarylamine mixtures used as a starting material is carried out in known manner by condensing aromatic amines with formaldehyde in the presence of equimolecular quantities or smaller quantities, even only catalytic quantities, of inorganic or organic acids such as hydrochloric acid, sulphuric acid, phosphoric acid, acetic acid or the like. The condensation of aromatic amines with formaldehyde may also be carried out by another known method which consists of heating these reactants to a high temperature in the presence of catalytic quantities of acid and inorganic salts such as sodium chloride or in the presence of carbon dioxide or even without catalysts. The resulting mixture contains a higher proportion of diaminodiarylmethanes or a higher proportion of polyaminopolyarylmethanes, depending on the molar ratio of arylamine to formaldehyde used. All these mixtures are suitable starting materials for the process according to the invention. Diaminodiarylmethane compounds which have been isolated by distillation or polyaminopolyarylmethanes which are left behind as distillation residue and only contain small quantities of diaminodiarylmethane compounds are also suitable for use as starting materials.

The amine used as starting material for the condensation with formaldehyde to prepare the polyaminopolyarylmethanes used according to the invention may be any arylamine of the general formula

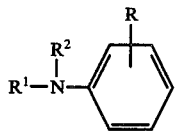

in which
R, R¹ and R² having the meanings indicated above.

The following are examples of such amines: aniline, o-chloroaniline, m-chloroaniline, p-chloroaniline, o-bromoaniline, m-bromoaniline, p-bromoaniline, o-anisidine, m-anisidine, p-anisidine o-phenetidine, m-phenetidine, p-phenetidine, o-toluidine, m-toluidine p-toluidine, 2-ethylaniline, 2-isopropylaniline, 2,6-diethylaniline N-methylaniline, N-ethylaniline, N-propylaniline, N,N-dimethylaniline, o-benzylaniline, m-benzylaniline, p-benzylaniline, α-naphthylamine and the like. The preferred amine is aniline.

The polyaminopolyarylmethane mixtures used for the process according to the invention preferably contain up to 10% by weight of dinuclear, 20 to 60% by weight of trinuclear, 20 to 45% by weight of tetranuclear and 5 to 20% by weight of higher nuclear polyaminopolyarylmethanes. In a special embodiment of the process according to the invention, however, a diaminodiarylmethane mixture consisting predominantly of the 4,4'-isomers may be used as starting material, a considerable proportion of the 4,4'-isomer being converted into the corresponding 2,4'-isomer. In this special embodiment, the process according to the invention does not serve to convert polyaminopolyarylmethanes having more than two arylamino groups into diaminodiarylmethanes but solely to convert 4,4'-isomers into 2,4'-isomers.

The aromatic monoamine which is used in mixture with the polyaminopolyarylmethane which has been obtained by amine/formaldehyde condensation may be any amine of the general formula

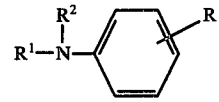

in which R, R¹ and R² have the meanings already indicated above and in which at least one ortho or para position to the amino groups is unsubstituted.

The amines already mentioned above are examples of such amines and again aniline is the preferred amine used for this purpose.

The process according to the invention is carried out by mixing the reactants and introducing them either batchwise or continuously into a pressurized reactor to maintain the liquid phase and heating to a temperature of between 220° C and 350° C. The proportion by weight of aromatic amine to polyaminopolyphenylmethane used as reactants is not critical and may lie between 1:1 and about 20:1 but may also be above or below these limits. The larger the excess of aromatic amine used, the greater is the degree of conversion of polyaminopolyphenylmethanes into diaminodiphenylmethanes. For this reason it is preferred to employ the reactants in proportions of between about 3:1 and 15:1.

The quantity of water used is also not critical and may vary from below 1% by weight to above 300% by weight of the amine mixture used for the reaction; it is preferably between 5 and 100% by weight.

The reaction temperature must be above 220° C to ensure a sufficiently rapid reaction. It is normally uneconomical to employ temperatures above 350° C and moreover side reactions are sometimes observed at such high temperatures. The temperatures employed are preferably between 260° C and 340° C and more particularly between 270° C and 320° C.

The reaction time or residence time in the reactor depends on the reaction temperature employed and the desired degree of conversion. It may vary between a few minutes and several hours. The higher the temperature employed and the lower the degree of conversion required, the shorter will be the reaction time and vice versa. The pressure is normally equal to the vapor pressure required to keep the reactants in the liquid phase but the reaction may also be carried out under the pressure of an inert gas. The reaction mixture is worked up by frictional distillation. In cases where the process is carried out continuously, this distillation may be carried out in one or more thin layer evaporators or distillation columns arranged in series.

The diaminodiphenylmethanes prepared by the process according to the invention are generally mixtures of 2,2'-diaminodiarylmethanes, 2,4'-diaminodiarylmethane and 4,4'-diaminodiarylmethane in which the proportion of 2,2'-isomers and 2,4'-isomers is considerably higher than in the diamine components present in the starting mixture. The process according to the invention is therefore of particular technical interest for the production of mixtures of diaminodiphenylmethane isomers which have a high 2,4'-diaminodiphenylmethane content by reacting polyphenylpolyamines with aniline in accordance with the invention because such mixtures of diaminodiphenylmethane isomers can be converted into very valuable diisocyanate mixtures by phosgenation for use in making polyurethane and other isocyanate based plastics. These mixtures of diisocyanato diphenylmethane isomers which have a high 2,4'-isomer content are distinguished by their low tendency to crystallization compared with that of 4,4'-diisocyanatodiphenylmethane which crystallizes readily. The amines obtainable by the process according to the invention are also suitable for producing polyureas or for use as hardeners for epoxide resins.

The examples described below were carried out in autoclaves which had been carefully cleaned and boiled several times with the reaction mixture under the reaction conditions.

EXAMPLES

EXAMPLE 1

A mixture of 1000 g of aniline, 105 g of polyaminopolyphenylmethanes containing less than 1% by weight of diaminodiphenylmethane and 300 g of distilled water is heated to 330° C. for 4 hours. When the reaction product is then worked up by distillation, 96 g of diaminodiphenylmethanes (12.8% 2,2'-isomers 60.2% 2,4'-isomers and 24.8% 4,4'-isomers; 2.2% by-products) and 22 g of residue are obtained. This corresponds to 79% conversion.

EXAMPLE 2

A mixture of 1000 g of aniline, 150 g of polyaminopolyphenylmethanes containing less than 1% by weight of diaminodiphenylmethane and 370 g of water is kept at 280° C for 30 minutes. Working up the reaction product yields 19 g of diaminodiphenylmethanes and 135 g of polyaminopolyphenylmethanes as distillation residue. The yield of product obtained by decomposition is therefore 10% of the theory. If the reactants are kept at 280° C for 60 minutes, the yield is 59% (12.7% 2,2'-isomer; 43.7% 2,4'-isomer and 42.4% 4,4'-isomer; 1.2% by-products).

EXAMPLE 3

A mixture of 500 g of o-toluidine, 64 g of polyaminopoly(methylphenyl)-methane prepared from o-toluidine containing less than 1% by weight of diaminodimethylphenylmethane and 200 g of distilled water is heated to 320° C for 120 minutes. 24 g of residue are obtained after distilling off the o-toluidine and diaminodimethyldiphenylmethane. This corresponds to a yield by decomposition of 62%.

EXAMPLE 4

If the process is carried out in a manner analogous to Example 3 using a poly-(N-methyl)-polyamino-polyphenylmethane which contains di-(N-methyl)-diaminodiphenylmethane in an amount of less than 1% by weight of N-methylaniline, the yield obtained from the decomposition reaction is 21%.

EXAMPLE 5

A mixture of 75 g of polyaminopolyphenylmethane containing less than 1% by weight of diaminodiphenylmethane, 500 g of 2,6-dimethylaniline and 185 g of water is kept at 320° C for 4 hours. Fractional distillation yields 36 g of diaminodiphenylmethane and 47 g of polyaminopolyphenylmethane, which corresponds to a yield of about 37%.

EXAMPLE 6

(a) A mixture of 1000 g of aniline, 150 g of polyaminopolyphenylmethanes with a diaminodiphenylmethane content of less than 1% by weight of aniline and 370 g of water is heated to 320° C for 3 hours. The yield obtained from the decomposition reaction is 71%.

(b) The residue obtained from 6a) is used and subjected to decomposition in analogous manner, with a yield of 65% (17.5% 2,2'-isomer, 55.5% of 2,4'-isomer and 25.6% of 4,4'-isomer; 1.4% by-products).

(c) When the residue obtained from 6b) is again decomposed, the yield obtained is 56%.

The starting compound (150 g) from 6a) has therefore been decomposed with a total yield of over 90%.

EXAMPLE 7

(a) A mixture of 1000 g of aniline, 150 g of polyaminopolyphenylmethanes containing less than 1% by weight of diaminodiphenylmethane and 350 g of water is kept at 320° C for 4 hours. The decomposition yield is 73% (5.9% 2,2'-isomer, 60.0% 2,4'-isomer and 32.3% 4,4'-isomer; 1.6% by-products).

(b) When the experiment is repeated at 350° C, the decomposition yield is 88% (10.6% 2,2'-isomer, 64.0% 2,4'-isomer and 21.3% 4,4'-isomer; 4.1% by-products).

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A process for the production of diaminodiarylmethanes which contain an improved proportion of 2,4'-diaminodiarylmethanes by heating polyaminopolyarylmethanes in the liquid phase with an aromatic monoamine which has at least one free position in the ortho- or para-position to the amino group, characterized in that the reaction is carried out solely in the presence of water.

2. The process of claim 1 wherein the reaction is conducted at a temperature of above 220° C.

3. The process of claim 1 wherein the monarylamine is aniline.

4. The process for converting 4,4'-diphenylmethane diamine into 2,4'-diphenylmethane diamine which consists of heating in water the said 4,4'-isomer with an aromatic monoamine which is unsubstituted in at least one position ortho to the amino group or para to the amino group to a temperature of above 220° C.

* * * * *